United States Patent [19]
Cook et al.

[11] Patent Number: 5,811,970
[45] Date of Patent: Sep. 22, 1998

[54] ELECTROMAGNETIC TEST FOR MICROSTRUCTURE ANOMALIES SUCH AS ALPHA-CASE, AND FOR CARBIDE PRECIPITATES AND UNTEMPERED AND OVERTEMPERED MARTENSITE

[75] Inventors: Kevin H. Cook, Farmingdale; John J. Munyak, Nesconset, both of N.Y.; William H. Pember, Palm City, Fla.

[73] Assignee: Northrop Grumman Corporation, Los Angeles, Calif.

[21] Appl. No.: 644,778

[22] Filed: May 10, 1996

[51] Int. Cl.$^6$ .................. G01N 27/90; G01R 33/12
[52] U.S. Cl. .................. 324/233; 324/227; 324/240
[58] Field of Search .................. 324/202, 209, 324/227, 232, 233, 234, 236–242

[56] References Cited

U.S. PATENT DOCUMENTS

| | | | |
|---|---|---|---|
| 3,159,784 | 12/1964 | Haslett et al. | 324/233 |
| 3,302,105 | 1/1967 | Libby et al. | 324/233 |
| 4,230,987 | 10/1980 | Mordwinkin | 324/233 X |
| 4,746,858 | 5/1988 | Metala et al. | 324/209 X |
| 4,897,518 | 1/1990 | Mucha et al. | 324/233 X |
| 4,947,117 | 8/1990 | Buck et al. | 324/227 |
| 5,028,100 | 7/1991 | Valleau et al. | 324/233 X |
| 5,140,264 | 8/1992 | Metala et al. | 324/227 X |

*Primary Examiner*—Gerard R. Strecker
*Attorney, Agent, or Firm*—Terry J. Anderson; Karl J. Hoch, Jr.

[57] ABSTRACT

An electromagnetic or eddy-current test for microstructure anomalies such as alpha-case in titanium alloys, and for carbide precipitates and untempered and overtempered martensite in steel alloys. The inspection is designed to provide an accurate, reproducible, cost effective, and nondestructive approach to detect and isolate discrepant parts exhibiting an unsatisfactory microstructural condition. The test method utilizes high frequency eddy-current test equipment, having an eddy-current test probe and a display screen, on a reference metallurgical standard to establish a reference level trace signal of phase amplitude response therefor on the display screen. The high frequency eddy-current test equipment is then utilized on a metallurgical sample being tested for the presence of the deleterious structural condition, to derive a trace signal of phase amplitude response therefor on the display screen. The level of the trace signal of phase amplitude response screen for the reference standard is compared on the display with the level of the trace signal amplitude response for the metallurgical sample being tested, to determine if the metallurgical sample has the particular deleterious condition for which it is being tested. The test method can use both acceptable and nonacceptable reference metallurigical standards to establish reference level trace signals of phase amplitude response therefor on the display screen.

10 Claims, 2 Drawing Sheets

ELECTROMAGNETIC TEST FOR MICROSTRUCTURE ANOMALIES SUCH AS ALPHA-CASE, AND FOR CARBIDE PRECIPITATES AND UNTEMPERED AND OVERTEMPERED MARTENSITE

BACKGROUND OF THE INVENTION

1. Field of the Invention

The present invention relates generally to an electromagnetic test for microstructure anomalies such as alpha-case in titanium alloys, and also for carbide precipitates and untempered and overtempered martensite in steel alloys. More particularly, the subject invention pertains to an electromagnetic test for such deleterious structural conditions which utilizes eddy-current test equipment, and compares the phase amplitude response of at least one metallurgical sample being tested with the phase amplitude response of a metallurgical test standard, such as a test sample which is known to be acceptable.

2. Discussion of the Prior Art

The unacceptable conditions and presence of both untempered and overtempered martensite in steel are generally a result of improperly administered high temperature, heat generating processes such as grinding and drilling.

Two methods are presently known in the prior art for detecting both untempered and overtempered martensite in steel alloys. The first known method involves a complete microstructural metallurgical analysis consisting of the sequential steps of sectioning, mounting, and performing microscopy on the inspected steel parts. This prior art method is destructive in nature, and also is very time consuming and expensive. The second known method involves the use of an acidic etchant composition. The acidic etchant method is relatively inexpensive in comparison with the first method, but is qualitative in result, and is often not suitable to the accessibility or geometry of the test site.

Prior to the development of the approach of the present invention, the only effective method in the prior art to detect the deleterious presence of carbide precipitate grain boundaries in steel alloys was through metallurgical microscopy, similar to the detection of untempered and overtempered martensite in steel. This method was costly, time consuming, and destructive in nature.

Alpha-case is generally produced as an unacceptable surface condition in titanium alloys. The alpha-case (or oxygen enriched layer) is formed when the titanium is improperly subjected to excessive heat in such processes as fabricating, machining, and welding.

The present method employed in the prior art for the detection and measurement of alpha-case in titanium involves the destructive sectioning, metallurgical mounting, and microscopic evaluation of the subject part, similar to the detection of untempered and overtempered martensite in steel and the detection of carbide precipitates. This process is time consuming and very cost prohibitive. General practices also involve regular chemical milling operations associated with ensuring against a detrimental alpha-case condition. The subsequent environmental aspects of the resultant chemical wastes of these practices is becoming more and more serious, all of which would be eliminated by the eddy-current test procedures of the present invention.

The present inventive method can be employed for the detection of microstructural anomalies such as, but not limited to, alpha-case, grain boundary depletion of chemicals and precipitation, embrittlement mechanisms, tin diffusion, eutectic melting, decarbonization, high temperature oxidation, etc. The detection of such microstructural anomalies generally involves the destructive sectioning of the subject part as described hereinabove. This process is both extremely time consuming and expensive.

Eddy-current testing equipment is very well known in the art, and is commercially available from a number of different equipment manufacturers such as Hocking and Nortec. However up to now, eddy-current (or electromagnetic) test equipment has only been utilized for the detection of flaws in materials such as cracks, in corrosion studies, and in heat treatment inspections such as inspections following tempering of metallurgical parts.

SUMMARY OF THE INVENTION

Accordingly, it is a primary object of the present invention to provide an electromagnetic or eddy-current test for microstructure anomalies such as alpha-case in titanium alloys, and for carbide precipitates and untempered and overtempered martensite in steel alloys. The subject invention utilizes eddy-current test equipment and compares the phase amplitude response of a metallurgical sample being tested with the phase amplitude response of at least one metallurgical test standard, such as a test sample which is known to be acceptable.

The inspection performed by the present invention is designed to provide an accurate, reproducible, cost effective, and nondestructive approach to detect and isolate discrepant parts exhibiting an unsatisfactory microstructural condition.

The utilization of an electromagnetic or eddy-current principle test for the measurement of an alpha-case layer in titanium alloys is novel in its entirety and should serve to save the titanium industry millions of dollars in averted testing costs.

The present invention involves a novel approach of utilizing electromagnetic field, eddy-current testing, and provides a very cost effective quality testing method to industry. The subject invention can be used for detection wherever deleterious metallurgical conditions are suspected to be present, such as microscope anomalies (e.g. alpha-case in titanium alloys), or carbon precipitates, or untempered and overtempered martensite in steel alloys.

As one consequence of a failure investigation involving what proved to be unsatisfactory defective parts, a test methodology has been developed to detect and sort out discrepant parts in a cost effective and nondestructive manner.

A further object of the subject invention is to employ an electrically generated field, commonly referred to as an eddy-current field, to detect the presence, magnitude and severity of deleterious microstructural surface conditions in steels, commonly referred to as both untempered and overtempered martensite. The conditions of both untempered and overtempered martensite in steel are generally derived through incorrectly performed process related operations, and can now be ascertained in a reliable and nondestructive manner which has not been possible in the prior art. Utilizing a high frequency eddy-current technique and correlating reference standards, a test can be performed which measures the level of phase amplitude response, which in turn reflects the electrical conductivity and impedance changes within the subject steel structure, thereby obtaining a quantified degree of the discrepant conditions.

The eddy-current test method can be used to detect: 1) the presence, magnitude and degree of severity of a deleterious oxygen enriched surface (alpha-case) for titanium structures, generally derived through detrimental process related operations; 2) the presence, magnitude and degree of severity of deleterious carbide precipitate grain boundaries in steel alloys, generally derived through detrimental process related operations; 3) the presence, magnitude and degree of severity of untempered and overtempered martensite in steel alloys, generally derived through improperly performed process related operations; and 4) the presence, magnitude, and degree of severity of many deleterious microstructural anomalies, generally derived through deleterious process related operations.

Employing an eddy-current test results in tremendous cost savings in unnecessary replacement charges. The present invention incorporates the basic principles of eddy-current testing, and applies them as never before used in the prior art for the detection of a number of deleterious structural conditions in metallurgical structures, which are generally the result of deleterious and improperly performed process related operations on the metallurgical structures.

In accordance with the teachings herein, the present invention provides an electromagnetic, eddy-current test method for testing for the presence of a deleterious structure condition in a metallurgical sample. The test method utilizes high frequency eddy-current test equipment, having an eddy-current test probe and a display screen, and at least one reference metallurgical standard to establish a reference level trace signal of phase amplitude response therefor on the display screen. The high frequency eddy-current test equipment is also utilized on a metallurgical sample being tested for the presence of the deleterious structural condition, to derive a trace signal of phase amplitude response therefor on the display screen. The level of the trace signal of phase amplitude response for the reference standard is compared on the display screen with the level of the trace signal of phase amplitude response for the metallurgical sample being tested, to determine if the particular deleterious condition being tested for is present in the metallurgical sample.

In greater detail, the electromagnetic, eddy-current test method can utilize an acceptable reference metallurgical standard to establish a reference level trace signal of phase amplitude response therefor, and can also utilize an unacceptable reference metallurgical standard to establish a reference level trace signal of phase amplitude response therefor.

The electromagnetic, eddy-current test method can be used for testing for the presence of a microstructure anomaly such as the presence of alpha-case in titanium alloys, or for carbide precipitates in steel, or for untempered and overtempered martensite in steel. For tests for a microstructure anomaly, the eddy-current test equipment can be operated in the frequency range of 300 KHz to 2 MHZ, depending upon the particular microstructure anomaly being tested for. For tests for the presence of alpha-case in titanium alloys, the frequency is typically around 2 MHZ. For tests for carbide precipitates in steel alloys, the frequency range is typically 300 to 500 KHz. For tests for untempered or overtempered martensite in steel alloys, the frequency is typically around 1 MHZ.

BRIEF DESCRIPTION OF THE DRAWINGS

The foregoing objects and advantages of the present invention for an electromagnetic test for microstructure anomalies such as alpha-case, and for carbide precipitates, and for untempered or overtempered martensite, may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 4:
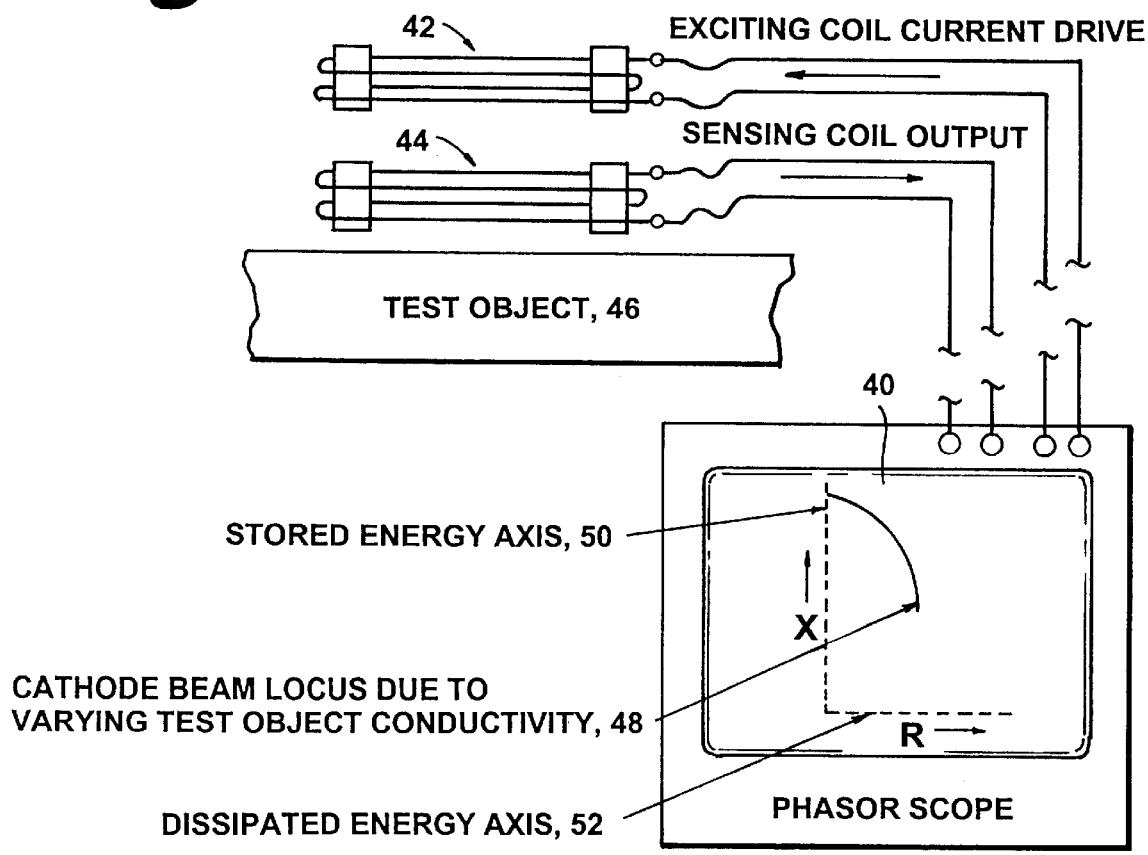
FIG. 4 is a schematic illustration of typical eddy-current test equipment, illustrating a control console display, and an eddy-current exciting coil and sensing coil positioned adjacent to a test object.

Referring to the drawings in detail and in particular to FIG. 4 initially, FIG. 4 is a schematic illustration of typical eddy-current test equipment, illustrating a control console display 40, an eddy-current primary or exciting coil 42, and an eddy-current secondary pickup or sensing coil 44. The two coils 42 and 44 are generally combined in a single eddy-current test probe, shown positioned schematically adjacent to a test object 46. FIG. 4 also illustrates a display of the eddy current test coil output loci 48 on a complex plane of voltages or impedances.

As is well known in this art, the impedance of a sensing coil, near test objects of various thicknesses and conductivities, varies in a manner somewhat similar to that of a test coil encircling a thin-walled tube. The resultant test signals are analyzed from their locus curves on the complex plane diagrams.

Locus curves for coil impedance or pickup coil voltage show test signal amplitude and phase (or time lag). In these complex plane diagrams, the inductive or stored energy effects are shown vertically along axis 50. Resistive or energy loss effects are shown as horizontal displacements along a dissipated energy axis 52. Changes in test frequency or in test material characteristics cause the test points to move along curves or loci on the complex plane diagrams. Eddy-current test equipment generally comprises a cathode ray oscilloscope and auxiliary circuits. The auxiliary circuits provide excitation current for the eddy-current test coil, signal amplifiers, signal nulling or AC bridge adjustment circuits, and synchronizing signals for deriving the cathode ray beam deflection signals.

In one exemplary embodiment, the eddy-current test procedure of the present invention was used for the inspection of stainless steel fitting nuts. The fitness of the subject parts was first brought into question by the failure of nuts on a duct assembly part. The failed fitting nuts were found to have an unsatisfactory sensitized and brittle microstructure, exhibiting a definitive carbide precipitate grain boundary. An incorrect heat treatment had been performed by the manufacturer, and was determined to be the cause of the brittle intergrannular presence.

The inspection performed by the present invention is designed to provide an accurate, reproducible, cost effective, and nondestructive approach to detect and isolate discrepant parts exhibiting an unsatisfactory microstructure.

The following represents an exemplary written test procedure which was generated for the inspection of the stainless steel fitting nuts referred to above, and is instructive on the general teachings of the present invention.

In preparation and cleaning of the stainless steel fitting nuts, all dirt, grease and debris is initially removed from the inspection area. Cadmium plated parts are manually lightly wet sanded with 220 grit cloth backed sandpaper on the most easily accessible area of one of the six side flat surfaces on the hexagonal portion of the fitting nut. All visible traces of any cadmium plating are thoroughly removed so as to not deleteriously affect the subsequent eddy-current test procedure. Once sanding has begun, the cadmium plating will appear to have a more silvery white appearance than the underlying base metal.

The required equipment and materials include:

a) an eddy-current flaw detector phase/amplitude apparatus, such as a Hocking Model AV-100;

b) eddy-current probes, leads, and associated adapters, surface probe (pencil) with 2" working area, rated at 500 KHz, 0.188" diameter terminating at 0.130" diameter, probe #3551F, as is available commercially from Nortec;

c) Teflon tape;

d) high temperature marking paint, applied through the use of cotton swabs or tapered brush;

e) 1" wide 220 grit cloth back sandpaper (used with water);

f) an eddy-current reference standard kit, comprised of three distinct material/process conditions, as listed below:

1. standard #1, "431 SS Cond A" (raw stock) Mil-S-18732, heat treated IAW Mil-H-6875, to HRC-40 min.

2. standard #2, acceptable NAS coupling, as proven through metallurgical analysis and microstructural evaluation.

3. standard #3, unacceptable NAS coupling (improper heat treatment).

The equipment and materials listed above were used to develop this procedure. Equipment and materials substitutions producing equivalent results may also be used.

During the calibration procedure:

1. Apply the Teflon tape to the face of the eddy-current probe.

2. Connect the probe to the instrument as per the manufacturers instructions.

3. Set the frequency of the eddy-current test equipment to 300 KHz.

4. Place probe on Std. #1; null/balance the instrument and adjust the signal trace to 20% screen height shown as Std. #1 in FIG. 1.

5. Adjust the instrument controls so that the signal trace is in the horizontal position.

Hocking AV-100 settings:

1. KHz—300
2. DB—49.5
3. phase angle 186.5
4. Aux Display—Std.
5. Store—Std.
6. Alarm—Off
7. Level—50
8. HP—Std.
9. LP—2
10. I/P—Std.
11. Y:X—2.1

6. Place the probe on standard #2. The trace on the display should match that represented by Std. #2 in FIG. 1, which represents a response from an acceptable part, starting at approximately 30% screen height.

7. Place the probe on standard #3. The trace on the display should match that represented by Std. # 3 in FIG. 1, which is a response from an unacceptable part, starting at approximately 50% screen height.

Evaluate the signal response as follows:

1. Signals appearing on the screen below the trace position of standard #3 are considered acceptable, and are marked with the high temperature marking paint, by means of a cotton swab or tapered brush. Note that the marking should not exceed ¼" in diameter.

2. Signals appearing on the screen above the trace position of standard #3 are considered unsatisfactory.

3. Signals appearing on the screen at the trace position of standard #3 must be further evaluated by the testing of all of the remaining and accessible flat areas. If subsequent testing reveals signal responses below that of the initial trace, the part disposition is satisfactory and should be marked accordingly; however if the subsequent testing displays responses at the initial trace level or above, the part disposition is unsatisfactory.

For cadmium plated parts, additional verification is also required when the initial signal response shows an acceptable condition. At that time the test operator selects one other surface, sands as required, and retests. If the signal continues to remain acceptable, the fitting is then satisfactory and should be marked accordingly.

Signals appearing below that of standard #2, and standard #1 are also considered satisfactory.

Repeat the calibration procedure prior to each new part tested.

Teflon tape should be removed when signs of wear are evident, or at a minimum of every 10 fittings tested. At that time new Teflon tape shall be used, and affixed to probe.

For each condition which is tested for utilizing an eddy-current test approach, the test operator must select appropriate eddy-current operating conditions. For example, the above test procedure for carbide precipitate group boundaries uses an operating frequency of 300 kHz. In general the operating frequency might be selected to be in the range of several hundred kilohertz to several megahertz, with the higher frequencies being proportional to the depth of the test area in the metallurgical sample. The depth of the test area in the metallurgical sample can be extended from 1 or 2 ten thousandths to 6 thousandths of an inch.

Figure 1:
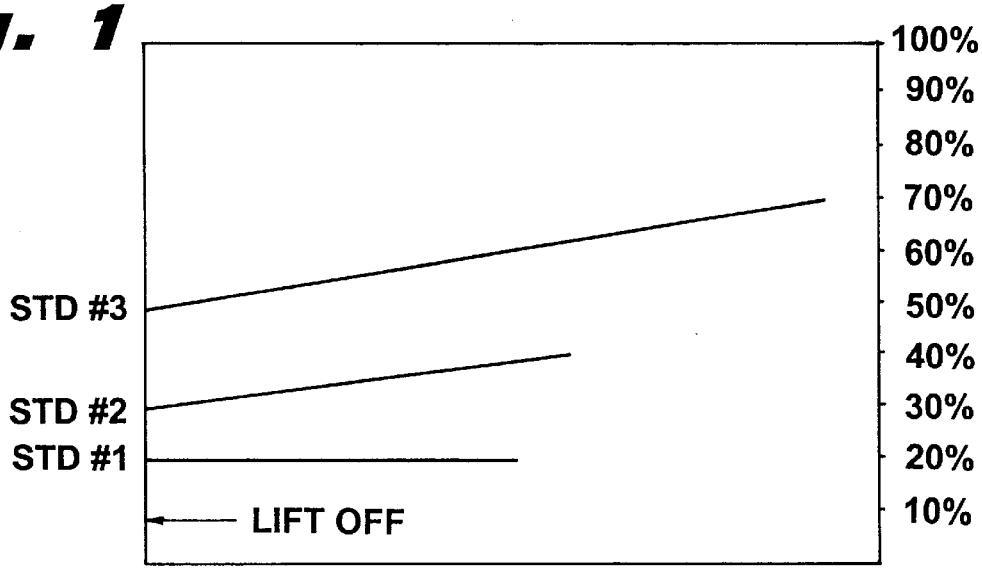
FIG. 1 illustrates exemplary waveforms illustrating display response trace signals useful for testing a metallurgical sample part for carbide precipitate grain boundaries, and shows a first reference response (STD #1) used to null balance the instrument, a second reference response (STD #2) for an acceptable reference metallurgical standard starting at 30% screen height, and a third reference response (STD #3) for an unacceptable part starting at 50% screen height.

FIG. 1 also illustrates a lift-off arrow, which indicates the direction of the trace, and is useful in setting up the equipment, as is generally known in the art. In FIG. 1, the abscicca is indicative of the surface conductivity of the metallurgical sample and also the depth of penetration of the eddy-currents into the metallurgical sample, and the ordinate is the phase amplitude, as is generally known in the art. In using eddy current equipment, the operator must take into consideration such factors as the particular type of test probe being utilized, and also other factors such as edge effects, which is the effect of an edge in proximity to the test probe on the resultant traces.

Figure 2:
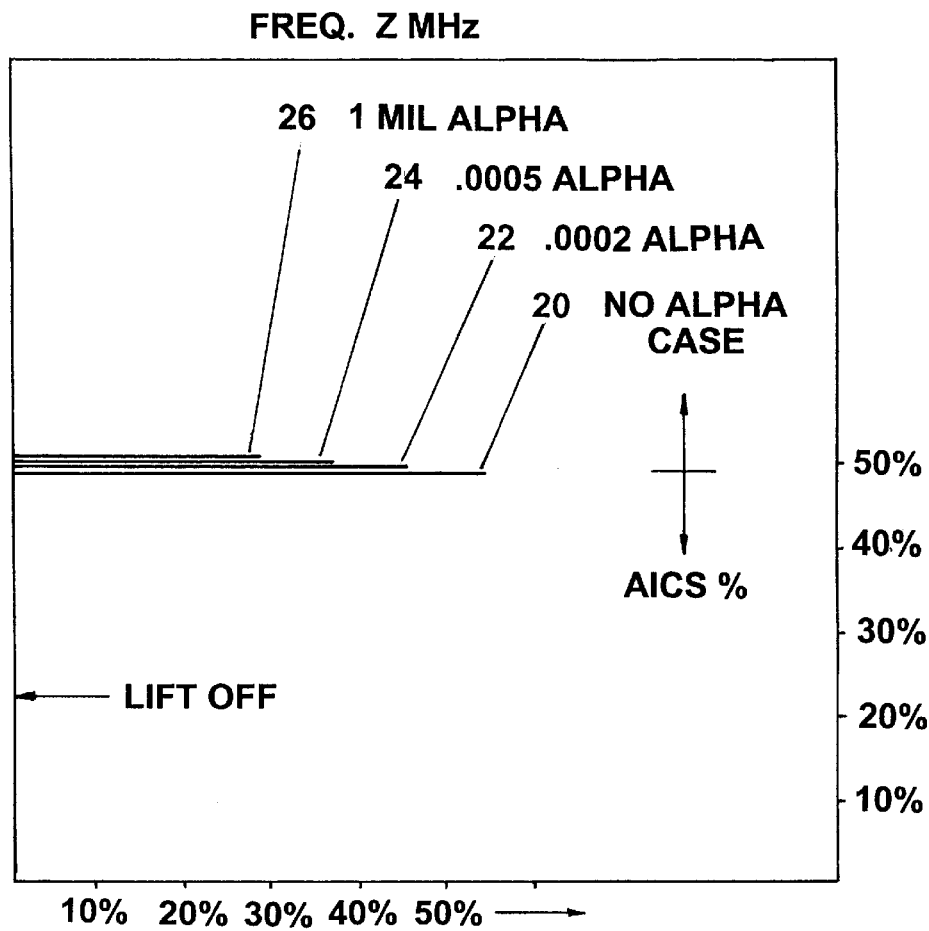
FIG. 2 illustrates exemplary waveforms illustrating display response trace signals useful for testing a metallurgical sample part for alpha-case, and shows four separate standard traces, a first trace for no alpha-case, a second trace for the presence of a layer of 0.0002 inch thickness alpha-case, a third trace for the presence of a layer of 0.0005 inch thickness alpha-case, and a fourth trace for the presence of a layer of 1 mil thickness alpha-case.

FIG. 2 illustrates exemplary waveforms display response trace signals useful for testing a metallurgical sample part for alpha-case, and shows four separate standard traces, a first trace 40 for no alpha-case, a second trace 42 for the presence a layer of 0.0002 inch thickness alpha-case, a third trace 44 for the presence of a layer of 0.0005 inch thickness alpha-case, and a fourth trace 46 for the presence of a layer of 1 mil thickness alpha-case. The standards are for operation at a nominal frequency of 2 MHZ. The four traces are basically substantially similar, differing primarily in the lengths thereof along the abscissa, which in FIG. 2 is the conductivity percentage. Layers of alpha-case, which are on the surface of the metallurgical test piece, basically function to separate the test probe from the underlying conductive titanium base, and so increased thicknesses of alpha-case layers result in lower conductivity percentages, as illustrated by the four traces in FIG. 2. FIG. 2 also illustrates a crossed line and arrow, labeled AICS% which represents a null point for the test equipment and traces.

Figure 3:
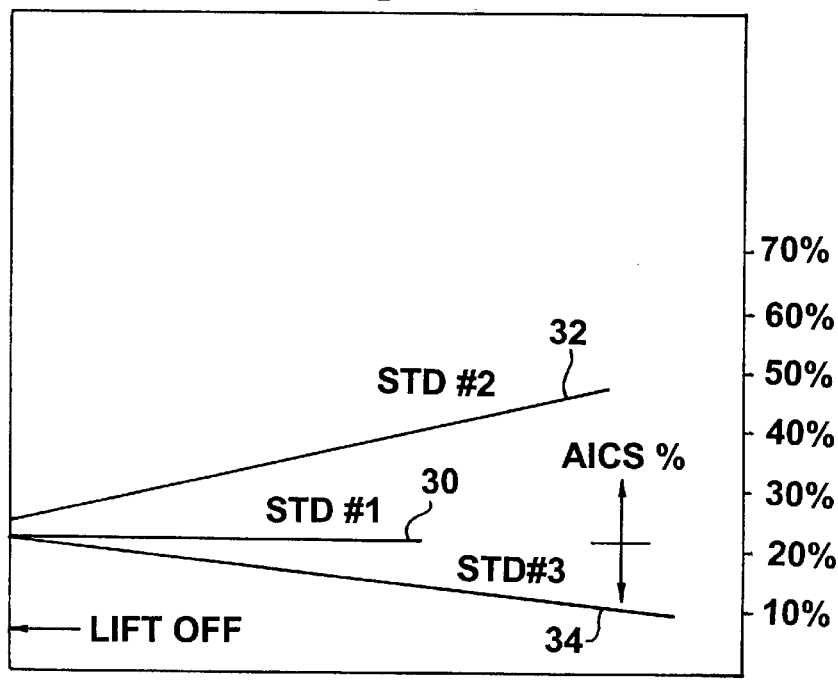
FIG. 3 illustrates exemplary waveforms illustrating display response trace signals useful for testing a metallurgical sample part tested for untempered and overtempered martensite, and shows a first standard response for an acceptable reference metallurgical standard having no overtempered martensite or untempered martensite at 20% screen height, and a second standard response for overtempered martensite and a third standard response trace for untempered martensite.

FIG. 3 illustrates exemplary waveforms illustrating display response trace signals useful for testing a metallurgical sample part tested for untempered and overtempered martensite, and shows a first standard response 30 for an acceptable reference metallurgical standard having no overtempered martensite or untempered martensite at 20% screen height, a second standard 32 for overtempered martensite, and a third standard response trace 34 for untempered martensite. The standards are for operation at a nominal frequency of 1 MHZ.

For eddy-current tests for untempered or overtempered martensite in steel, the operating frequency is typically selected to be around 1 MHZ. For eddy-current tests for microstructure anomalies, the operating frequency might be selected to be in the range of 300 KHz to 2 MHz, depending upon which type of microstructure anomaly is being tested for. Generally, a lower operating frequency results in increased depth of penetration of the eddy-current signals into the metallurgical sample.

In general, each eddy-current test relies upon comparing a trace on the CRT screen for a tested metallurgical sample with a trace on the CRT screen derived from one or more test standards, which are certified or have been tested to establish that they are quality standard samples free of the particular metallurgical defect being tested for.

While several embodiments and variations of the present invention for an electromagnetic test for microstructure anomalies such as alpha-case, and for carbide precipitates and untempered and overtempered martensite are described in detail herein, it should be apparent that the disclosure and teachings of the present invention will suggest many alternative designs to those skilled in the art.

What is claimed:

1. An electromagnetic, eddy-current test method for testing for the presence of a deleterious microstructural metallurgical condition in the upper surface microstructure of a metallurgical sample, comprising:

a. utilizing high frequency eddy-current test equipment, having an eddy-current test probe and a display screen, operated at a frequency above 300 KH$_z$, on a reference metallurgical standard to establish a reference level trace signal of phase amplitude response therefor on the display screen;

b. utilizing the high frequency eddy-current test equipment, operated at a frequency above 300 KHz, on a metallurgical sample being tested for the presence of deleterious structural condition, to derive a trace signal of phase amplitude response therefor on the display screen;

c. comparing the level of the trace signal of phase amplitude response on the display screen for the reference standard with the level of the trace signal on the display screen for the phase amplitude response for the metallurgical sample being tested, to determine if the metallurgical sample has a deleterious microstructural metallurgical condition present.

2. An electromagnetic eddy-current test method as claimed in claim 1, further including utilizing the high frequency eddy-current test equipment on an acceptable reference metallurgical standard to establish a reference level trace signal of phase amplitude response therefor on the display screen.

3. An electromagnetic eddy-current test method as claimed in claim 2, further including utilizing the high frequency eddy-current test equipment on an unacceptable reference metallurgical standard to establish a reference level trace signal of phase amplitude response therefor on the display screen.

4. An electromagnetic eddy-current test method as claimed in claim 1, further including utilizing the high frequency eddy-current test equipment on a metallurgical sample being tested for the presence of a microstructure anomaly, to derive a trace signal of phase amplitude response therefor on the display screen.

5. An electromagnetic eddy-current test method as claimed in claim 4, including utilizing the high frequency eddy-current test equipment on a titanium alloy sample being tested for the presence of alpha-case in the titanium alloy, to derive a trace signal of phase amplitude response therefor on the display screen.

6. An electromagnetic eddy-current test method as claimed in claim 5, wherein the eddy-current test equipment is operated at a frequency of substantially 2 MHZ.

7. An electromagnetic eddy-current test method as claimed in claim 1, including utilizing the high frequency eddy-current test equipment on a steel metallurgical sample being tested for the presence of a carbide precipitates, to derive a trace signal of phase amplitude response therefor on the display screen.

8. An electromagnetic eddy-current test method as claimed in claim 7, wherein the eddy-current test equipment is operated in the frequency range of 300 to 500 KHz.

9. An electromagnetic eddy-current test method as claimed in claim 1, including utilizing the high frequency eddy-current test equipment on a steel metallurgical sample being tested for the presence of untempered or overtempered martensite, to derive a trace signal of phase amplitude response therefor on the display screen.

10. An electromagnetic eddy-current test method as claimed in claim 9, wherein the eddy-current test equipment is operated at a frequency of substantially 1 MHZ.

\* \* \* \* \*